United States Patent
Kawakami et al.

(10) Patent No.: US 8,394,933 B2
(45) Date of Patent: Mar. 12, 2013

(54) PROTEIN REFOLDING COLUMN FILLER AND COLUMN

(75) Inventors: Masayuki Kawakami, Kanagawa (JP); Tatsuo Tsunoda, Ibaraki (JP); Hideaki Togashi, Ibaraki (JP); Takayuki Nara, Ibaraki (JP); Shun-ichi Matsuura, Miyagi (JP); Chisato Sekikawa, Ibaraki (JP); Akiko Kawai, Ibaraki (JP); Akiyoshi Kawata, Ibaraki (JP); Fujio Mizukami, Miyagi (JP); Kengo Sakaguchi, Ibaraki (JP)

(73) Assignee: FUJIFILM Corporation, Tokyo (JP)

( * ) Notice: Subject to any disclaimer, the term of this patent is extended or adjusted under 35 U.S.C. 154(b) by 285 days.

(21) Appl. No.: 12/593,713

(22) PCT Filed: Apr. 4, 2008

(86) PCT No.: PCT/JP2008/000877
§ 371 (c)(1),
(2), (4) Date: Mar. 26, 2010

(87) PCT Pub. No.: WO2008/126400
PCT Pub. Date: Oct. 23, 2008

(65) Prior Publication Data
US 2010/0210820 A1 Aug. 19, 2010

(30) Foreign Application Priority Data
Apr. 5, 2007 (JP) .................................. 2007-099284

(51) Int. Cl.
*C07K 1/16* (2006.01)
*G01N 33/538* (2006.01)
*A61K 38/00* (2006.01)

(52) U.S. Cl. ..................... 530/415; 530/390.5; 530/350; 530/300; 436/541

(58) Field of Classification Search .................. None
See application file for complete search history.

(56) References Cited

U.S. PATENT DOCUMENTS

| | | | | |
|---|---|---|---|---|
| 5,306,487 A | * | 4/1994 | Karapasha et al. | 424/76.6 |
| 5,733,272 A | * | 3/1998 | Brunner et al. | 604/359 |
| 6,402,958 B1 | * | 6/2002 | Moran | 210/656 |
| 7,417,003 B2 | * | 8/2008 | Schmidt et al. | 502/63 |
| 2006/0194279 A1 | * | 8/2006 | Mizukami et al. | 435/69.1 |

FOREIGN PATENT DOCUMENTS

| | | |
|---|---|---|
| JP | 2004-330113 A | 11/2004 |
| JP | 2005-29531 A | 2/2005 |
| JP | 2005-192452 A | 7/2005 |
| JP | 2005-220121 A | 8/2005 |
| JP | 2005-281267 A | 10/2005 |
| WO | 2005/005459 A1 | 1/2005 |

OTHER PUBLICATIONS

Kang Y et al., "Uniform Nanozeolife Microspheres with Large Secondary Pore Architecture", Chemistry of Materials, vol 18. No. 7, Apr. 4, 2006, pp. 1861-1866, XP002587200.
Hiroyuki Chiku et al., "Zeolites as new chromatographic carriers for proteins—easy recovery of proteins adsorbed on zeolites by polyethylene glycol", Analytical Biochemistry, vol. 318, Jul. 1, 2003, pp. 80-85, XP002391719.
Tosheva L et al., "Zeolite beta spheres", Microporous and Mesoporous Materials, vol. 48, No. 1-3, Nov. 1, 2001, pp. 31-37, XP004332124.
Baojian Zhang et al., "Starch Gel Templating of Spongelike Macroporous Silicalite Monoliths and Mesoporous Films", Chemistry of Materials, American Chemical Society, vol. 14, No. 3, Mar. 1, 2002, pp. 1369-1375, XP002414825.
Lipkind B A et al., "Forming of synthetic zeolotes with binder additives into microbead granules", Chemistry and Technology of Fuels and Oils, vol. 23, No. 10, Oct. 23, 1987, pp. 476-478, XP002587201.
Matsui M et al., "Selective adsorption of biopolymers on zeolites", Chemistry—A European Journal, vol. 7, No. 7, Jan. 1, 2001, pp. 1555-1560, XP002981855.
Chiku, et al., "A novel protein refolding method using a zeolite", Anal. Biochem., 2006 vol. 348, No. 2, pp. 307-314.
International Preliminary Report on Patentability dated Oct. 15, 2009 on PCT/JP2008/000877.
Office Action dated Aug. 7, 2012 in Japanese Application No. JP 2009-508911.
R. L. Waterman et al, Pelletization of Natural, Sedimentary Zeolite Fines, 4th International Symposium on Agglomeration, 1986, pp. 357-366.

* cited by examiner

*Primary Examiner* — Manjunath Rao
*Assistant Examiner* — Samuel Liu
(74) *Attorney, Agent, or Firm* — Sughrue Mion, PLLC

(57) ABSTRACT

It is an object of the present invention to provide: a protein refolding column filler, which is effective for the refolding, namely, the activation of the function, of an inactive protein with an as yet unformed higher order structure produced in *Escherichia coli* or the like, or a protein whose conformation has been changed due to a certain cause and which has become inactivated; and a column filled with the aforementioned column filler. The present invention provides a protein refolding column filler, which comprises zeolite with BEA structure (Zeolite Beta) that is granulated into a particle state.

9 Claims, 3 Drawing Sheets

PROTEIN REFOLDING COLUMN FILLER AND COLUMN

TECHNICAL FIELD

The present invention relates to an agent for activating the function of an inactive protein. More specifically, the present invention relates to: a certain type of device such as a column, which has the ability to refold an inactive protein whose higher order structure has not been formed or a protein whose conformation has been changed due to a certain cause and which has become inactivated, and to activate and/or regenerate the original function of such protein; and activation of an inactive protein, namely, manufacturing and/or production of an active protein, utilizing such device. For example, in such technical fields as production of biochemical products and pharmaceutical products, the present invention usefully provides: a novel device capable of refolding a protein with an as yet unformed higher order structure that has been produced using a gene expression system such as *Escherichia coli*, and activating the original function and/or activity of the protein; and a novel method for activating the function of the protein utilizing such device. Conventionally, a protein obtained in an expression system such as *Escherichia coli* has been problematic in that it generally has a disordered conformation, and in that it does not have its original function and/or physical properties and as a result, it does not exhibit activity. The device of the present invention does not only provide an innovative technique of manufacturing and/or producing proteins, which activates the function and/or activity of inactive proteins including the above-described proteins as typical examples and regenerate such proteins to proteins with desired function and/or activity, but it also significantly simplifies the process of the aforementioned technique, in comparison with the conventional technique.

BACKGROUND ART

An object that actually acts and works in vivo is not a gene, but a protein produced from such gene. Accordingly, clarification and/or analysis of the function and/or structure of a protein are directly associated with, for example, the treatment of disease or drug discovery, and thus are extremely important. Thus, the synthesis and/or production of various types of proteins by various methods, the analyses of the structures of the obtained proteins, and clarification of the mode of action and role of each protein in vivo have vigorously been progressing. At present, it has been well known that the function of a protein is determined not only based on an amino acid sequence constituting it and/or a chain length thereof, but also based on an ordered conformation (higher order structure) obtained from such sequence and/or chain length.

In general, a protein is synthesized using an expression system such as *Escherichia coli*, insect cells, or mammalian cells. A protein obtained by such synthesis using insect cells or mammalian cells may adopt a controlled higher order structure and an ordered conformation, and may have solubility in many cases. However, such protein synthesis method using insect cells or mammalian cells is disadvantageous in that it is highly expensive and it takes a long period of time to obtain a protein of interest due to extremely complicated separation and purification operations, and also in that the amount of a protein obtained is extremely small. In contrast, in the case of a protein synthesis method using *Escherichia coli*, operations are simple, it does not take a long period of time to obtain a protein of interest, and it does not cost much. Accordingly, at current, a method using *Escherichia coli*, into which a genetic code for the synthesis of a protein of interest has been incorporated, is mainly applied to protein synthesis, and the production process thereof is being established.

When a protein of a higher organism such as a human is synthesized using an *Escherichia coli* expression system, the protein can be obtained as designed, in terms of the binding order of amino acids or the number of amino acids bound, namely, an amino acid chain length. However, the conformation of the obtained protein is disordered, and the higher order structure thereof is not controlled. That is to say, the obtained protein is an insoluble protein known as an "inclusion body," in which an amino acid chain is entangled. This inclusion body of insoluble protein naturally lacks the desired functions and properties and lacks activity. As a result, an *Escherichia coli*-based production process requires the refolding of the inclusion body, that is, a process in which the inclusion body is unraveled and converted to a soluble protein with a modulated higher order structure and an ordered conformation.

This type of refolding can be applied not only to a protein produced by *Escherichia coli*, but to regeneration of a protein that is inactivated by a certain mechanism such as thermal history, and thus it is an extremely important technique. This refolding has been under very active investigation, and different methods have been proposed. Almost all of these methods involve a batch process. Thus, these methods have a low refolding rate and frequently can do nothing more than sporadically give desirable results for certain limited proteins (in particular, for specific low molecular weight proteins). At present, there are no methods for carrying out such refolding, which are universal and general methods applicable to a variety of proteins and which are efficient and economical, providing a high refolding rate.

Under such circumstances, the present inventors have studied a phenomenon whereby a biopolymer selectively adsorbs on an inorganic oxide such as zeolite (see Non-Patent Document 1). During this process, the inventors have found that an inactive protein can be activated by adsorption on and desorption from Zeolite Beta, thereby completing an invention relating to a method for activating the function of an inactive protein using Zeolite Beta (see Patent Documents 1, 2, 3, and 4, and Non-Patent Document 2). However, the methods described in Patent Documents 1, 2, 3, and 4, and Non-Patent Document 2 involve a batch process, and Zeolite Beta is generally obtained in the form of an ultrafine powder particle (a submicron or smaller). Thus, in a separation step in a process in which a protein is allowed to adsorb on or desorb from Zeolite Beta, it is not easy to carry out filtration, and a centrifugal separator must be used many times. The protein activation process of the aforementioned invention has been extremely simple, and it has only utilized adsorption on and desorption from Zeolite. However, this process has been disadvantageous in that the process itself has been complicated and has required time and efforts.

In addition, it has been essential for the conventional refolding operation and/or process to use a centrifugal separator as well as chromatography. Such chromatography has also required time and efforts, and it has resulted in a major problem regarding expensiveness.

[Patent Document 1] JP Patent Publication (Kokai) No. 2005-29531 A

[Patent Document 2] JP Patent Publication (Kokai) No. 2005-192452 A

[Patent Document 3] JP Patent Publication (Kokai) No. 2005-220121 A

[Patent Document 4] JP Patent Publication (Kokai) No. 2005-281267 A

[Non-Patent Document 1] Chem. Eur. J., Vol. 7 (2001) 1555-1560

[Non-Patent Document 2] Anal. Biochem., Vol. 348 (2006) 307-314

DISCLOSURE OF THE INVENTION

Problems to be Solved by the Invention

It is an object of the present invention to provide: a protein refolding column filler, which is effective for the refolding, namely, the activation of the function, of an inactive protein with an as yet unformed higher order structure produced in *Escherichia coli* or the like, or a protein whose conformation has been changed due to a certain cause and which has become inactivated; and a column filled with the aforementioned column filler.

Means for Solving the Problems

The present inventors have conducted intensive studies directed towards achieving the aforementioned object. As a result, the inventors have found that zeolite with BEA structure (Zeolite Beta), which has a refolding function to modulate an inactive protein having a disordered higher order structure so as to convert it to an active protein and which is granulated into a particle state, can be used as a filler for a protein refolding column, thereby completing the present invention. The protein refolding column filler of the present invention can be applied by simple operations to the refolding of various types of proteins with disordered conformation including large proteins each having a molecular weight of more than 100,000, such as a protein with an as yet unformed higher order structure produced in an expression system such as *Escherichia coli* or a protein inactivated by a certain mechanism such as thermal history. Thus, according to the present invention, there is provided a general and universal technique of refolding a protein by easy and/or simple operations.

Thus, the present invention provides the following invention.

(1) A protein refolding column filler, which comprises zeolite with BEA structure (Zeolite Beta) that is granulated into a particle state.
(2) The refolding column filler according to (1), wherein Zeolite Beta is granulated into particles having a particle diameter between 20 and 1,000 μm.
(3) The refolding column filler according to (1) or (2), which consists of Zeolite Beta and a starch adhesive for granulation of the Zeolite Beta.
(4) The refolding column filler according to (3), wherein the starch adhesive for granulation of the Zeolite Beta is a material that does not affect a protein.
(5) The refolding column filler according to (3) or (4), wherein the content of the starch adhesive for granulation of the Zeolite Beta is 0.2% to 50% in a dry state of the starch adhesive.
(6) The refolding column filler according to (1) to (5), wherein the granulated Zeolite Beta has a controlled granular variation.
(7) The refolding column filler according to any one of (1) to (6), wherein a starch adhesive material is added to Zeolite Beta by spraying or dropping it to the material powders of the Zeolite Beta, while rotating and/or stirring them, and the obtained mixture is then granulated, so as to obtain the granulated Zeolite Beta.

(8) An open column filled with the protein refolding column filler of any one of (1) to (7).
(9) A column used in in-line incorporation, which is filled with the protein refolding column filler of any one of (1) to (7).
(10) The column according to (8) or (9), which is allowed to come into contact with a protein dispersed in a solution, so as to exhibit a protein-refolding function.
(11) A method for activating the function of an inactive protein, which comprises adding an inactive protein to a column filled with the protein refolding column filler of any one of (1) to (7), so as to allow the inactive protein to come into contact with the protein refolding column filler.

Effect of the Invention

The present invention relates to a refolding column filler that is a material having the ability to activate the function of an inactive protein, and a column. According to the present invention, the following effects can be achieved.
(1) A refolding column filler comprising zeolite with BEA structure (Zeolite Beta) as a universal substance or material for activating the original functions of a wide range of inactive proteins (regardless of the types of such inactive proteins) and a column can be selected.
(2) The aforementioned protein, for example, an inactive protein with an as yet unformed higher order structure produced in an expression system such as *Escherichia coli*, or a protein whose conformation has been changed due to a certain cause and which has become inactivated, is allowed to come into contact with the refolding column filler and column of the present invention, so that the original function and/or activity of the protein can be activated by refolding.
(3) The refolding column filler and column of the present invention also has an effect on an inclusion body protein, and thus they are useful for a method for efficiently refolding such inclusion body.
(4) A method of allowing an inactive protein to come into contact with the refolding column filler and column of the present invention to activate the function of the inactive protein is a general, universal, and efficient method with a high refolding rate, which can be applied to various types of denatured proteins, regardless of the chain length and/or sequence of amino acids constituting such protein.
(5) Zeolite Beta that constitutes the refolding column filler and column of the present invention is inexpensive.
(6) Various shapes of columns are available for a column that is filled with the refolding column filler of the present invention. Thus, such column is easily obtainable and inexpensive.
(7) A method for producing the refolding column filler of the present invention is also easy and inexpensive.
(8) The refolding column filler and column of the present invention and a method for activating the function of an inactive protein using such filler and column can be applied to the refolding of various types of proteins with a disordered conformation, including large proteins with a molecular weight of more than 100,000.
(9) For example, by combining a protein synthetic process using an *Escherichia coli* expression system with activation of the function of an inactive protein using the refolding column filler and column of the present invention, the higher order structure of the protein is modulated, and as a result, a novel process for producing an active protein having the original function thereof can be proposed and/or established.

BEST MODE FOR CARRYING OUT THE INVENTION

Next, the present invention will be described more in detail.

Zeolite with BEA structure (popular name: Zeolite Beta) that constitutes the refolding column filler of the present invention is also referred to as Beta Zeolite. Typical examples include: commercially available Zeolite Beta; Zeolite Beta synthesized and/or prepared in accordance with a publication (see Zeolites, Vol. 11 (1991) 202); Zeolite Beta obtained by sintering the aforementioned zeolites; Zeolite Beta which comprises ammonium or various types of aliphatic and/or aromatic ammoniums in spaces possessed by the aforementioned zeolites; skeleton-substituted Zeolite Beta, in which a portion of skeleton silicon forming the zeolite has been substituted with another type of metal; and skeleton-substituted Zeolite Beta comprising the aforementioned ammonium. All types of Zeolite Betas basically have the function and/or ability thereof, as long as they have the skeletal structure as Zeolite Beta. Thus, all types of Zeolite Betas can be used. A method for producing Zeolite Beta constituting the aforementioned refolding column filler and column and the properties of such Zeolite Beta are not particularly limited.

However, the function and/or ability of Zeolite Beta constituting the refolding column filler and column of the present invention are exhibited, when inactive and denatured proteins are allowed to come into contact with the zeolite, namely, when they are adsorbed on and/or desorbed from the zeolite. At the time, the affinity between the Zeolite Beta surface and the target protein becomes important. Moreover, adsorption and/or desorption of the protein is often influenced by a dispersion medium, a denaturant or a surfactant contained in the dispersion medium, a refolding factor, the pH of the dispersion medium, and the like. Accordingly, depending on the protein used as a target, the composition of a solution containing such target protein, and the like, the refolding ability of the refolding column filler and column of the present invention is somewhat varied. It depends on the aforementioned each different type of Zeolite Beta that constitutes such filler and column. Generally speaking, a refolding column filler constituted with Zeolite Beta containing ammonium has refolding ability higher than that of a refolding column filler constituted with Zeolite Beta containing no ammonium. Thus, the aforementioned refolding column filler and column are preferably constituted with Zeolite Beta containing ammonium and skeleton-substituted Zeolite Beta containing ammonium in many cases.

Examples of such ammonium contained in Zeolite Beta constituting the refolding column filler and column of the present invention include ammoniums easily remaining in spaces possessed by the zeolite. Specific examples of such ammoniums include: ammonium ions; mono, di, tri, and tetraalkylammonium ions such as those in which an alkyl group is methyl, ethyl, propyl, butyl, or the like; and ammonium ions of 5-, 6-, and 7-membered aliphatic amines and aromatic amines. More specific examples include a piperidinium ion, an alkylpiperidinium ion, a pyridinium ion, an alkylpyridium ion, an aniline ion, and an N-alkylaniline ion. Basically, any type of ammonium can be used herein, as long as it is able to enter pores possessed by Zeolite Beta. Thus, examples of such ammonium are not'limited to the aforementioned examples.

Elements that form the skeleton of Zeolite Beta constituting the refolding column filler and column of the present invention are generally, silicon and oxygen, or silicon, oxygen and aluminum. However, Zeolite Beta in which a portion of silicon or aluminum is substituted with another element, and substituted Zeolite Beta comprising the aforementioned ammonium in the pores thereof, also have the function to activate an in active protein. Typical examples of an element substitutable for the skeletal silicon or aluminum of Zeolite Beta include boron, phosphorus, gallium, tin, titanium, iron, cobalt, copper, nickel, zinc, chrome, and vanadium. However, examples are not limited thereto. Basically, any type of element may be used, as long as it does not destroy the structure of Zeolite Beta. In addition, with regard to the amount of an element substitutable for the skeletal silicon or aluminum of Zeolite Beta, such amount is not limited, as long as it is an amount that does not destroy the structure of Zeolite Beta. The aforementioned substituted Zeolite Beta can become a refolding column filler that exhibits the function to refold an inactive or denatured protein.

Zeolite Betas, which constitute the refolding column filler and column of the present invention, are substances that are all excellent in terms of thermostability and chemical stability, are inexpensive, and are friendly to the environment. Accordingly, the refolding column filler of the present invention and a column filled therewith are extremely useful for production of biochemical products, pharmaceutical products, and the like, and thus such filler and column may bring on unexpected economic effects.

In general, Zeolite Beta is obtained only in the form of an ultrafine powder particle of a submicron or less. Thus, the direct use of Zeolite Beta itself as a refolding column filler is often problematic. When ungranulated Zeolite Beta is filled into a column, for example, it is sufficiently anticipated that it will pass through a filter established on the outlet side of the column because of its small particle diameter, and it will thereby affect the pump portion of the device or easily clog the filter, and thus that it cannot be used as a column. Moreover, in order to fill a column with ungranulated Zeolite Beta and to allow a solution to pass through the column, high pressure is required. This is anticipated to add unnecessary burden to a solution-sending pump and the like. Taking into consideration the aforementioned circumstances, granulation of Zeolite Beta is essential to the use as a column filler. In the present invention, Zeolite Beta was granulated into a particle state, so as to develop a protein refolding column filler and a protein refolding column.

A protein refolding column may be configured such that a solution may permeate through the column at a suitable pressure. Thus, the particle diameter of Zeolite Beta used as a column filler is determined depending on the viscosity or concentration of a solution, the performance of a pump, and the like. Such particle diameter may be changed depending on usage or the form of usage, and it may be selected, as appropriate. If taking into consideration the pressure resistance of an actual column or the performance of a pump, it is desired that the particle diameter of Zeolite Beta used as a column filler is preferably set between 20 and 1,000 μm.

The refolding column filler of the present invention is preferably composed of zeolite with BEA structure called "Zeolite Beta" and a starch adhesive (a granulating agent) for granulating such Zeolite Beta. Generally speaking, such zeolite substance is poor in terms of self-sintering property, it is hardly molded by itself in many cases. Thus, in order to produce a granule, namely, in order to design and/or control the form and/or shape of the zeolite, a starch adhesive material may be used in granulation. Hence, the use of such starch adhesive material involves a lot of flexibility, and it is advantageous.

However, a method for designing and/or controlling the form and/or shape of granulated Zeolite Beta, namely, a method for producing granulated Zeolite Beta, is varied depending on the usage or the form of usage of the granule, and thus such method may be selected, as appropriate. Accordingly, all of known granulation methods can be applied to production of the aforementioned granule. Such known methods are not particularly limited, and they may be selected, as appropriate, or may be applied in combination. Moreover, such known methods do not need particularly specific explanation or reference. But to mention two or three examples of a method for producing the aforementioned granule, namely, a method for designing and/or controlling the form and/or shape of such granule, there are the following methods. Examples of a method for producing a granule used herein include: granulation of Zeolite Beta using an adhesive insoluble in water; production of Zeolite Beta in an aggregation state by a dry gel conversion method or a solid-phase conversion method (see Stud. Surf. Sci. Catal. Vol. 125 (1999) 1-12; and *Hyomen* (Surfaces), Vol. 37 (1999) 537-557); adhesion and/or molding of Zeolite Beta using inorganic powders such as alumina; granulation of Zeolite Beta by adhesion to a substance acting as a nucleus. However, examples are not limited thereto.

On the other hand, since zeolite is a substance that is extremely poor in terms of self-sintering property, it is significantly difficult to granulate such zeolite by sintering. In a case in which sintering is attempted, alumina is frequently used as a sintering additive. However, when alumina is used as such sintering additive, a thermal reaction progresses between zeolite and alumina, thereby forming a novel phase. Such novel phase is a substance that essentially differs from zeolite in many cases. Thus, it is highly likely that such novel phase is not adequate as a refolding column filler or that it does not have the function of such refolding column filler. Consequently, granulation of Zeolite Beta by this kind of sintering is not highly recommended, but it is not excluded, either.

As a preferred example of a granulation method using a starch adhesive material, a common granulation method using a pan-type granulator is well known. Material powders are filled into a pan-shaped container comprising an inclined rotation axis, and they were then stirred by rotation. Thereafter, a starch adhesive material is added by spraying or by drops to the material powders, so as to promote the aggregation and/or adhesion of the material powders, thereby carrying out granulation. The dimension and/or size of a pan, a rotation rate or an angle of inclination, a method and/or a rate for adding a starch adhesive material, and the like are changed, depending on a method utilizing the obtained granule, the form of usage, and the amount of granule produced, and thus such factors are selected, as appropriate.

The form and/or shape of the granule are appropriately selected from among a sphere, a mass, a scale, a pore, and the like, depending on a method utilizing the obtained granule and/or the form of usage. In particular, with regard to a starch adhesive material, any type of starch adhesive material may be used, as long as it is basically insoluble in water and it does not affect a protein. As a preferred example of such starch adhesive material, acetylcellulose or the like is favorable. An acetone solution of such acetylcellulose is favorably used. Nitrocellulose, polystyrene resin, and the like are also favorable. Such nitrocellulose is preferably used in a state in which it is dissolved in acetone or in a solvent comprising such acetone as a main ingredient. On the other hand, such polystyrene resin is preferably used in a state in which it is dissolved in a solvent comprising ethyl acetate as a main ingredient.

When Zeolite Beta is granulated by the aforementioned granulation method, granulation progresses as the additive amount of acetylcellulose increases, so that a greater particle diameter can be achieved. The additive amount of such starch adhesive material is not particularly limited. However, if an excessive amount of starch adhesive material is added, the surface of Zeolite Beta is covered with the starch adhesive material, and as a result, the function to refold a protein may be lost. Thus, a granule that is preferable as a refolding column filler can be obtained by setting the weight percentage of a starch adhesive material in a dry state at 0.2% to 50% based on the total weight of the filler, although it also depends on conditions for production of such granule.

From a practical viewpoint, it is extremely inconvenient if there is a performance difference among individual refolding columns. With regard to such performance difference among individual refolding columns, the granular variation of a filler, the shape of granule, and the like greatly influence on the amount of a filler filled, the filling state, and the condition. In order to solve such inconvenience, it is necessary to control the granular variation of the granule or the shape of granule. A method therefor depends on a method utilizing the obtained granule or the form of usage, and it is selected, as appropriate. Accordingly, all of known methods can be applied to the control of the granular variation of the granule or the shape of granule, and such methods are selected, as appropriate, or several methods are used in combination. Thus, the method for controlling the granular variation of the granule or the shape of granule is not particularly limited, and specific explanation or reference is not particularly necessary. The shape of the granule can be controlled by regulating conditions for granulation. In addition, common methods for controlling the granular variation of the granule include classification using a sieve and classification using a fluid. According to such classification method using a sieve, particle diameter distribution can be controlled in accordance with the specification of a sieve prepared.

The refolding column filler and column of the present invention target all of inactive proteins having an unmodulated higher order structure. The present refolding column filler and column particularly target proteins having a disordered conformation, which are obtained in an expression system such as *Escherichia coli*; namely, what are called, inclusion bodies, or proteins inactivated by a certain mechanism such as thermal history, or proteins artificially denatured using a denaturant. The refolding column filler and column of the present invention refold the conformation of the aforementioned protein in a process in which the protein adsorbs on and/or desorbs from the refolding column filler, so that they activate and/or give the original function to the aforementioned protein. The aforementioned ability of the refolding column filler and column is not necessarily limited to those as described above. Such ability is generally exhibited by the following operations. In other words, the function of an inactive protein is activated by the following operations. First, the protein is dispersed and dissolved in a solution containing a denaturant, a surfactant, and the like. Thereafter, the solution is poured, flown, or added dropwise into the present refolding column filler and column, so as to allow the protein to adsorb on the present refolding column filler. Subsequently, the protein is allowed to desorb from the present refolding column filler. These steps do not particularly require a separator such as a centrifugal separator.

In general, a protein is produced in an expression system such as *Escherichia coli*, and such protein is generally used in an aqueous solution in many cases, and even the protein is deactivated, the protein is present in an aqueous solution in many cases. Thus, as a dispersion medium for such protein before the protein has adsorbed on the refolding column filler and column, water is preferably used. However, the dispersion medium is not necessarily limited to water. Any type of dispersion medium can be basically used, as long as it does not react with the protein and it does not convert the confirmation of the protein to an unfavorable shape. In such a case, such medium may be used singly or in combination with water. Typical examples of this type of medium include monohydric and polyhydric alcohols and polyethers, but examples are not limited thereto.

Adsorption and desorption of the protein are carried out in the presence of a denaturant, a surfactant, a pH adjuster, a refolding factor, and the like, which are used to easily untangle or refold an entangled protein chain such as an inclusion body, and/or in the presence of a certain kind of reducing agent used to cleave an S—S bond unfavorably generated in such protein chain. Examples of such type of denaturant, surfactant, pH adjuster, and refolding factor include guanidine hydrochloride, trisaminomethane hydrochloride (Tris HCl), polyethylene glycol, cyclodextrin, 4-(2-hydroxyethyl)-1-piperazineethanesulfonic acid (HEPES), 2-morpholonoethanesulfonic acid (MES), 3-monopholinopropanesulfonic acid (MOPS), polyphosphoric acid, sucrose, glucose, glycerol, inositol, Dextran T-500, and Ficoll 400. However, examples are not limited to the aforementioned compounds. Any type of substance can be used, as long as it has the same action.

As a reducing agent for cleaving an unfavorably generated S—S bond and retaking the original structure, 2-mercaptoethanol is generally used because it is inexpensive and is easily procured. However, examples of such reducing agent are not limited thereto. All reducing agents having the same action, including a redox reagent as a representative example, can be used. Naturally, in a case in which a protein chain is easily untangled, or in a case in which an unfavorable S—S bond has not been generated, such denaturant, surfactant, and/or reducing agent are not necessarily used. Thus, the presence of these agents is not always essential, and they are appropriately selected and used, depending on situation. Moreover, in a case in which such agents are used, the amounts thereof are determined, as appropriate, depending on situation.

For desorption of the protein, substitutional adsorption is generally used. Basically, any operation can be applied, as long as it does not inhibit the activation of the function of the protein after desorption. Thus, the operation necessary for desorption is not particularly limited. Accordingly, pH change, temperature change, and the like can also be used, and further, such means can be used in combination with substitutional adsorption. Furthermore, conventionally, during substitutional adsorption, salts such as halogenated alkali or sodium dodecyl sulfate have been frequently used as a substance for promoting desorption of the protein in elution by column chromatography. There are many cases in which the combined use of such salts brings on significant effects. Accordingly, when desorption of the protein is carried out by substitutional adsorption, various types of salts such as those used in such column chromatography elution may be used in combination with a surfactant or a refolding factor. Salts for such combined use are not limited to those as mentioned above. Any types of salts can be used, as long as they do not inhibit the activation of the function of the protein after desorption. On the other hand, needless to say, if unnecessary, it is not necessary to add such salts.

When the aforementioned protein is desorbed from the refolding column filler and column of the present invention in a state in which it is refolded, the protein may be aggregated and precipitated depending on the concentration thereof or the composition or condition of a solution. In order to prevent such unfavorable aggregation and/or precipitation, there is used arginine whose effects are well known. However, a substance for preventing such aggregation and/or precipitation is not limited to arginine. Any type of substance may be used, as long as it has the same action as that of arginine Naturally, when the protein is hardly aggregated in a state in which it is refolded, or when unfavorable aggregation and/or precipitation do not occur, such aggregation preventing agent is not necessarily used. Thus, the presence of such preventing agent is not essential, and it is selected and used as appropriate, depending on situation. In addition, in a case in which such preventing agent is used, the amount of the agent used is determined as appropriate, depending on situation.

Furthermore, in order to promote adsorption of the protein on the refolding column filler and column of the present invention or desorption of the protein therefrom, various types of additional operations may be carried out in combination of the aforementioned operations. Typical examples of such additional operation include application of ultrasonic wave or microwave, and application of magnetic and electric fields. By the aforementioned procedures and/or operations, the ability of the refolding column and column filler to refold a protein is exhibited at a high level. As a result, a protein with an as yet unformed higher order structure produced in an expression system such as *Escherichia coli*, and a protein inactivated by a certain cause are refolded, and thereby the original function of such protein is rapidly activated.

The present invention will be specifically described based on the following examples. However, these examples are not intended to limit the scope of the present invention.

EXAMPLES

In the following examples, activation of the function of a protein produced in an *Escherichia coli* expression system and that of a denatured protein will be described. However, these examples are not intended to restrict and/or limit the scope of the present invention.

(1) Preparation of Column Filler and Column
(a) Production (Granulation) of Refolding Column Filler A Zeolite Beta powder was added into a pan-type granulator or a granulator whose pan-type portion had been replaced with a cylindrical portion, and an acetone solution containing 1%- to 2%-by-weight acetylcellulose was then sprayed thereon using an atomizer, an airbrush, or the like, so as to carry out granulation. The rotation rate of the granulator was set at 60 rotations/min, and the angle of inclination of the pan or the cylindrical container was set at 45 degrees. However, these conditions are controlled as appropriate, depending on the amount of the raw material powder filled and the like. The concentration of acetylcellulose is preferably 1% to 2% by weight. If the concentration is higher than the aforementioned range, the viscosity of the solution increases, and it becomes difficult to spray the solution. When the final concentration of acetylcellulose is set at 3% to 20% with respect to the weight of the raw material powder, a preferred granular powder can be obtained. As the content of acetylcellulose increases, the particle diameter tends to increase, naturally.

(b) Classification of Refolding Column Filler

Since the granulated Zeolite Beta has granular variation, it is classified. A common classification method using a sieve or the like can be applied. However, since Zeolite Beta has a small primary particle diameter and easily absorbs water content and the like in the air, it is easily aggregated. Thus, it is often difficult to carry out classification using an ordinary sieve. As a result, the granulated product is suspended in ultrapure water to form a slurry, and such slurry is then sieved, so as to facilitate classification in many cases. If Zeolite Beta has a particle diameter of 50 μm or more, it can easily be classified by this method. Particle diameter distribution can be controlled in accordance with the specification of a sieve prepared. For example, if powders that pass through a sieve of 100 μm but do not pass through a sieve of 75 μm are collected, the particle diameter distribution of such powders is between 75 and 100 μm. Particle diameter distribution can be controlled by the same method.

(c) Filling of Column with Refolding Column Filler

The produced granular Zeolite Beta is suspended in ultrapure water, and a refolding column is then filled with the suspension, utilizing spontaneous precipitation due to gravity. The column is further placed in a vacuum desiccator or the like, and a decompression treatment is then carried out for deaeration, so as to ensure a filled state containing no voids. The filling of a refolding column with Zeolite Beta that is in a dry state may be possible. However, taking into consideration usability in the future, the coexistence of Zeolite Beta with ultrapure water is more advantageous. Both an open column and an in-line column are filled with Zeolite Beta by the same above method. If Zeolite Beta has a tight range of granular variation, the same above filled state is realized utilizing spontaneous precipitation due to gravity, and a performance difference among individual columns can be reduced to minimum.

With regard to the filling of an open column with a filler, a representative column, Poly-Prep chromatography column manufactured by Bio-Rad Laboratories is used, and a filler that becomes a slurry state as a result of mixing with ultrapure water is poured therein in an amount of approximately 1 to 2 g (1 to 2 ml). By waiting for spontaneous precipitation due to gravity, the filler is stabilized. Thereafter, an outlet is opened at the lower portion of the column to waste redundant ultrapure water. The column is preserved or used in a wet state due to ultrapure water.

With regard to the filling of an in-line column with a filler, a representative column, Tricon column set manufactured by GE Healthcare is used. The column is connected with a glass tube having the same diameter via an adapter, and a filler that becomes a slurry as a result of suspension in ultrapure water is poured therein. By waiting for spontaneous precipitation due to gravity, the filler is stabilized. The adapter is removed, and a decompression treatment is then carried out in a state in which it is filled with ultrapure water, so as to perform deaeration. The column is preserved or used in a wet state due to ultrapure water.

For comparison, a column was filled with ungranulated Zeolite Beta. As a result, it became clear that a filter attached to the outlet side of the column is easily clogged, and that it became useless as a column. In addition, a large pressure was required for filling a column with ungranulated Zeolite Beta and allowing a solution to pass through the column. This resulted in adding unnecessary burden to a solution-sending pump and the like. Thus, it was demonstrated that granulation of Zeolite Beta is essential for the use thereof as a column filler.

(2) Preparation of Sample and the Like (a) Denatured Protein Solution

As proteins to be activated, RNaseA and lysozyme, which were available as agents, were used. In addition, as inclusion bodies expressed from *Escherichia coli*, GRP (green fluorescent protein) and LDH (lactate dehydrogenase) were used. These proteins, including reagents and inclusion bodies, were each dissolved in a 6 M guanidine hydrochloride solution, and while measuring concentrations, 1 mg/ml solutions were prepared.

(b) Refolding Buffer

As a general example, a solution having a composition of 50 mM HEPES (pH 7.5)/0.5 M NaCl/20 mM 2-mercaptoethanol/0.5 (w/v) % polyethylene glycol 20000 (a refolding factor)/1 (v/v) % Tween 20 (a surfactant) was used as a refolding buffer.

(3) Method for Measuring Concentration of Protein

A Bradford method and a BCA method were appropriately applied to the measurement of the concentration of a protein. Using a 1.5-ml tube and a microplate, certain operations were carried out, and the concentration of a protein was then determined by colorimetry using a calibration curve.

(4) Method for Measuring Activity of Protein (a) Evaluation of Lysozyme Activity The activity of lysozyme was evaluated using the bacteriolytic activity of *Micrococcus lysodeikticus* as an indicator. A freeze-dried cell mass of *Micrococcus lysodeikticus* was suspended in a 0.1 M phosphate buffer (pH 7.0), and it was then adjusted so that the absorbance at a wavelength of 450 nm became 1.0. The thus obtained solution was used as a reaction solution. After pre-incubation of the reaction solution at 25° C., a sample containing lysozyme was added to the reaction solution, and a decrease in the absorbance at a wavelength of 450 nm was then measured. The activity of decreasing the absorbance at a wavelength of 450 nm by 0.001 for 1 minute was defined as 1 unit, and an active value was calculated.

(b) Evaluation of RNaseA Activity

The activity of RNaseA was evaluated as follows. Cytidine 2',3'-cyclic monophosphate was dissolved in a 20 mM phosphate buffer (pH 7.5) so that the concentration thereof became 0.5 mg/ml. The obtained solution was used as a reaction solution. After pre-incubation of the reaction solution at 25° C., a sample containing RNaseA was added to the reaction solution, and an increase in the absorbance at a wavelength of 286 nm was then measured. The activity of increasing the absorbance at a wavelength of 280 nm by 0.001 for 1 second was defined as 1 unit, and an active value was calculated.

(c) Evaluation of GFP Activity

The activity of GFP (green fluorescent protein) was evaluated based on the intensity of fluorescence emitted by GFP. GFP in a 50 mM Tris-HCl buffer (pH 7.5) was excited with a wavelength of 490 nm, and the intensity of fluorescence observed at a wavelength of 510 nm was measured using a fluorospectrophotometer. The intensity of fluorescence emitted by the refolded GFP was calculated as a value relative to that of undenatured GFP having the same concentration, which was used as a control. The activity was then evaluated.

(d) Evaluation of LDH Activity

The activity of LDH (lactate dehydrogenase) was evaluated based on a decrease in NADH in a reaction catalyzed by LDH (pyruvic acid+NADH→lactic acid+NAD). Since NADH has absorption at a wavelength of 340 nm, the enzyme activity can be determined by measuring a decrease in the absorbance. A 100 mM MES buffer containing 0.1 mM NADH and 100 mM pyruvic acid was used as a reaction solution, and the reaction solution was pre-incubated at 30° C. for 10 minutes. Thereafter, a sample containing LDH was mixed with the reaction solution, and a decrease in the absorbance at a wavelength of 340 nm was then measured. The activity of decreasing the absorbance at a wavelength of 340 nm by 0.001 for 1 second was defined as 1 unit, and an active value was calculated.

(5) Refolding Using Open Column
(a) Refolding Example of GFP

An open column having an effective column portion of 0.8×4 cm was filled with 20 mg of a filler. In this case, a filler having a granular variation of 75 to 150 µm was used. After an outlet had been opened at the lower portion of the column, the open column was washed with 1 ml of a 6 M guanidine hydrochloride solution. Thereafter, 1 ml of a 6 M guanidine hydrochloride solution, in which 3 mg of GFP had been dissolved, was added dropwise to the open column. By this operation, GFP that was in a denatured state adsorbed on the filler. 10 ml of 1 mM Tris-HCl (pH 7.5) was added, and it was allowed to pass through the column to wash the filler. Thereafter, 2 ml of a refolding buffer was added to the column. The solution that was allowed to pass through the column was fractionated by 0.2 ml each. The recovered solution was left overnight, and thereafter, the concentration and activity of the protein were evaluated.

FIG. 1 shows the measurement results regarding the activity and concentration of each fractionated protein solution. In the figure, fraction Nos. 1-10 each correspond to 0.2 ml of the refolding buffer fractionated by allowing 2 ml of the refolding buffer to pass through the open column. The protein activity of each fraction, and the concentrations of the $3^{rd}$ to $6^{th}$ fractionated protein solutions are shown. From the GFP concentration in each fractionated solution, it is found that, even in the case of each of the $3^{rd}$ to $6^{th}$ fractionated solutions, approximately 20% GFP was recovered from the filler. GFP that is refolded in such fraction and is then recovered has a relatively high protein concentration, and it ensures accuracy in evaluation. Thus, the activity of the protein was evaluated based on fluorescence intensity. The refolded GFP emitted fluorescence with intensity of approximately 600 to 1,100 LU (LU: unit for indicating the relative intensity of fluorescence). Hence, it is found that the refolded GFP regained an activity of approximately 20%, with respect to the fluorescence intensity of undenatured GFP with the same concentration (approximately 5,000 LU). It is found that the GFP refolded with the aforementioned column filler favorably regained its activity.

(b) Refolding Example of Lysozyme

An open column having an effective column portion of 0.8×4 cm was filled with 500 mg of a filler. In this case, a filler having a granular variation of 300 to 500 µm was used. After an outlet had been opened at the lower portion of the column, the open column was washed with ultrapure water. Thereafter, 5 ml of a 6 M guanidine hydrochloride solution, in which 5 mg of lysozyme had been dissolved, was added dropwise to the open column. By this operation, the ultrapure water was substituted with the lysozyme solution, so that lysozyme that was in a denatured state adsorbed on the filler. 1 ml of a 6 M guanidine hydrochloride solution was added, and thus the filler was washed therewith via the column. Further, 2 ml of ultrapure water was allowed to pass through the column to wash the filler. Thereafter, a refolding buffer was added to the column. Total 5 ml was added, and the solution that was allowed to pass through the column was fractionated by 1 ml each. The concentration and activity of the protein contained in the recovered solution were evaluated.

The concentration of each fractionated protein solution was measured. Although depending on the speed of supplying the solution to the column, when 1 ml of the solution was added dropwise to the column for approximately 15 minutes, 70% or more of lysozyme adsorbed and retained on the filler. When the dropping rate was increased, the amount of lysozyme unadsorbed tended to increase. An almost amount of adsorbed protein was recovered by allowing the refolding buffer to pass through the column. The activity of the thus refolded lysozyme was evaluated based on bacteriolytic properties. As a result, the bacteriolytic activity of the lysozyme was confirmed.

FIG. 2 shows the measurement results regarding the specific activity and concentration of lysozyme contained in the recovered solution. In the figure, F1 to F5 each indicate the numerical value of lysozyme that was refolded and recovered. It is found that it exhibits a specific activity of 60 to 100 units/mg. It is found that the activity was recovered by refolding operations. An aliquot of lysozyme contained in 5 ml of the 6 M guanidine hydrochloride solution, in which 5 mg of lysozyme had been dissolved, was allowed to pass through the open column (corresponding to FT in the figure). Such lysozyme was poor in terms of the recovery of activity, although it was in a relatively large amount. Thus, it is found that lysozyme, on which the refolding operation had been performed using the present column filler, was better in terms of the recovery of activity.

(6) Refolding Using In-Line Column
(a) Standard Operational Method

A glass column, both ends of which are hermetically closed with seals and which has the function of connecting with a tube, and the like are used. As a typical example, a Tricon column set manufactured by GE Healthcare, a Tricon 5/20 column, was used. 150 mg of a filler, which has been granulated and classified in the range between 75 and 100 µm, is converted to a slurry using ultrapure water, and it is filled into the column. This column is equipped into FPLC, for example, AKTA10S manufactured by GE Healthcare. Using the pump of the FPLC apparatus, a protein solution is allowed to pass through the column at a certain rate. The protein is allowed to adsorb on the filler, and the column is then washed with ultrapure water or the like. Thereafter, a refolding buffer is allowed to further pass through the column, so as to recover the protein. The solution that has been allowed to pass through the column is generally fractionated using a fraction collector and then recovered. The concentration and activity of the protein in the recovered solution are evaluated.

(b) Refolding Example of LDH

LDH as an inclusion body expressed in *Escherichia coli* is dissolved in a 6 M guanidine hydrochloride solution containing a suitable denaturant buffer, so as to prepare a 1 mg/ml protein solution. First, a denaturant buffer containing no proteins is allowed to pass through a column for equilibration. Thereafter, 10 ml of the protein solution is allowed to pass through the column at a flow rate of 0.3 ml/min, so that the protein is allowed to adsorb on the column. Thereafter, the column is washed with a denaturant buffer, and it is further washed with a washing buffer containing no guanidine hydrochloride, so as to wash out impurities such as an unadsorbed protein as well as the denaturant buffer. Subsequently, a refolding buffer is allowed to pass through the column, so as to recover the protein.

FIG. 3 shows a graph corresponding to a series of operations. The solid line indicates the concentration of a protein contained in the solution discharged from the column, which is calculated based on absorption of ultraviolet light at a wavelength of 280 nm. The broken line indicates the results obtained by measuring the activity of an aliquot fractionated from the recovered protein solution. It is found that, first, adsorption is saturated by allowing the protein solution to pass through the column, and that the protein is gradually discharged. It is found that, next, unadsorption or elution of impure substances is confirmed in the washing process, and that such substances do not exhibit activity. The protein is recovered by supplying the refolding buffer to the column, and it can also be confirmed that the protein has recovered its activity. That is to say, it was confirmed that a protein dissolved in a denaturant buffer adsorbed on a column filler, and that, after washing, the refolded active protein was then recovered by supplying a refolding buffer for substitution with the previous buffer. In the case of RNaseA and GFP as well, the protein can be recovered by the same above operations. Although depending on determination of conditions or the total amount to be handled, these operations are completed for several tens of minutes to several hours.

As described in the aforementioned examples, it became clear that the original activities of several proteins are rapidly obtained by extremely easy operations, using a protein refolding column filler and a column. The protein refolding column filler and column of the present invention are useful as a general and universal protein refolding column filler and column, which can be applied to various types of proteins such as a protein with an as yet unformed higher order structure, a denatured protein and/or an inactive protein. The application of the protein refolding column filler and column of the present invention is not limited to the proteins described in the examples, but they can also be applied to any given proteins.

INDUSTRIAL APPLICABILITY

The present invention relates to a protein refolding column filler useful for activation of the function of an inactive protein, and a column filled with the aforementioned column filler. According to the present invention, the original function and/or activity of an inactive protein with an as yet unformed higher order structure produced in an expression system such as *Escherichia coli*, or a protein whose conformation has been changed due to a certain cause and which has become inactivated, can be activated by refolding. This method is useful as a method for efficiently and easily refolding an inclusion body. Moreover, according to the present invention, there can be provided a general, universal, and efficient protein refolding column filler with a high refolding rate, which can be applied to various types of proteins. Zeolite Beta that constitutes the protein refolding column filler used in the present invention is a substance that is inexpensive and is friendly to the environment. The protein refolding column filler of the present invention is effective for the refolding of various types of proteins with a disordered conformation, including large proteins each having a molecular weight of more than 100,000. Accordingly, by a further development, for example, by combining a protein synthetic process using an expression system of *Escherichia coli* with the protein refolding column filler of the present invention and the usage thereof, there can be constructed novel protein production process and/or system for producing a protein having the original function specific thereto and having a modulated higher order structure.

Figure 1:
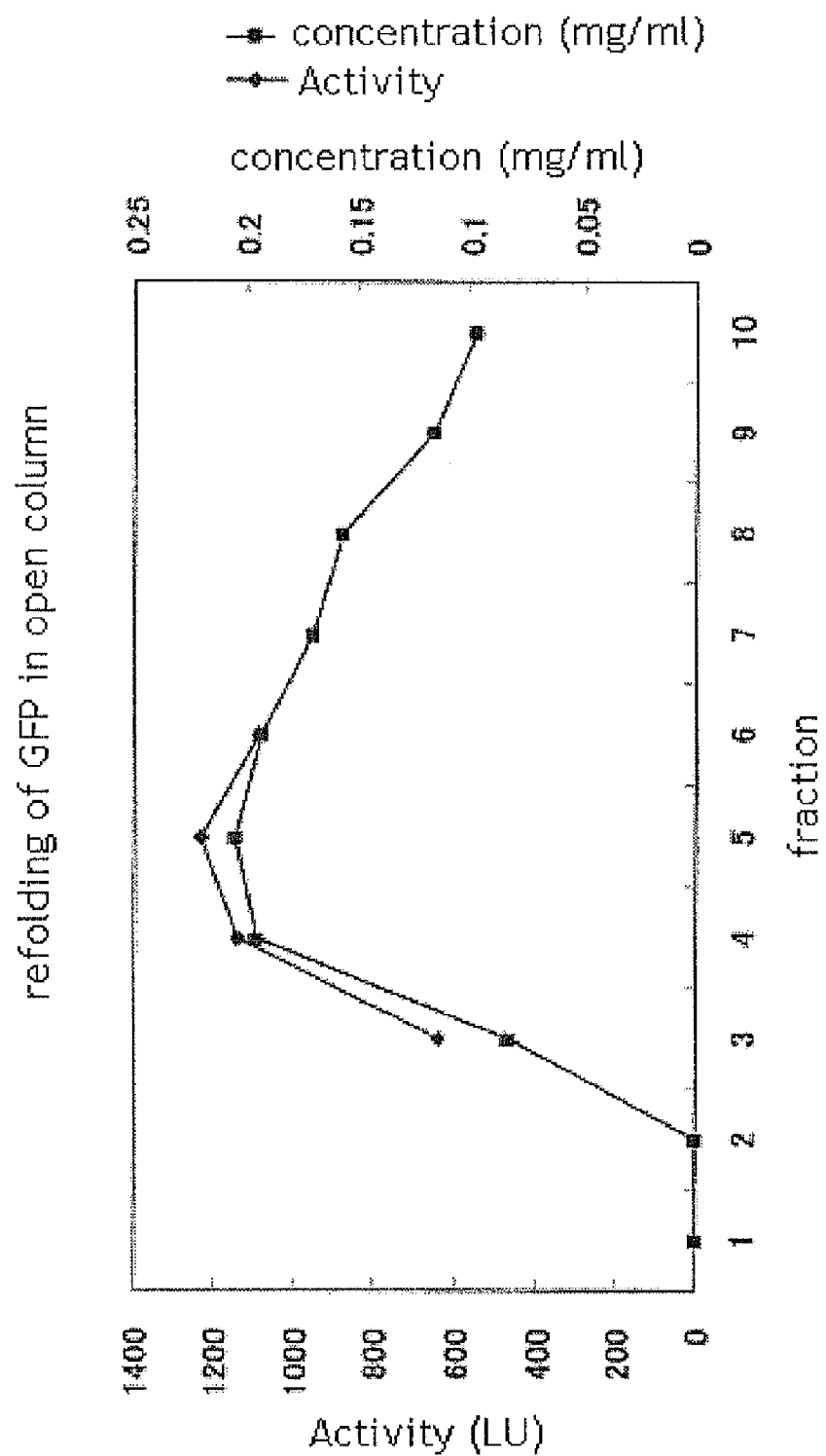
FIG. 1 shows the refolding of GFP using an open column.
Figure 2:
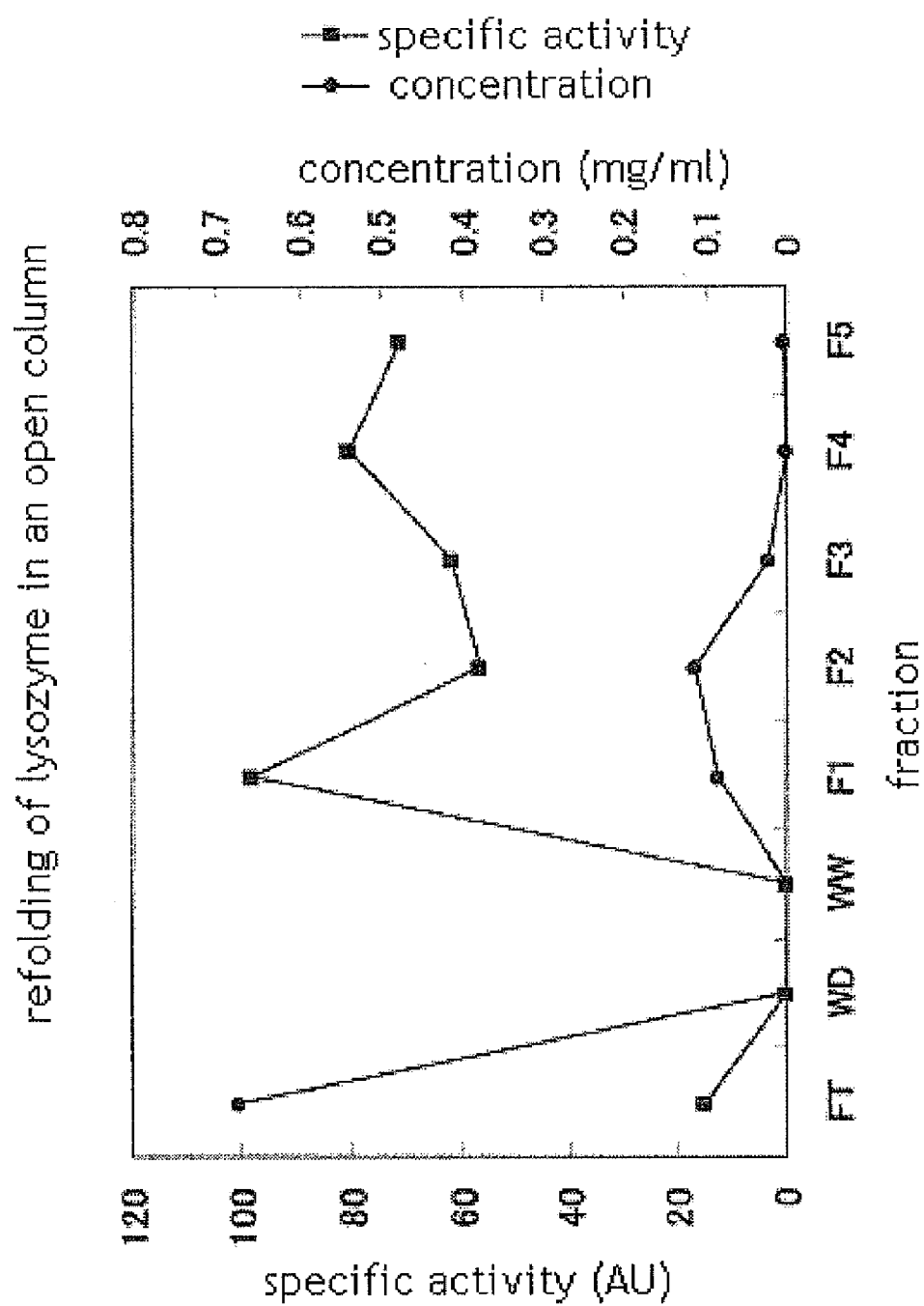
FIG. 2 shows the refolding of lysozyme using an open column.
Figure 3:
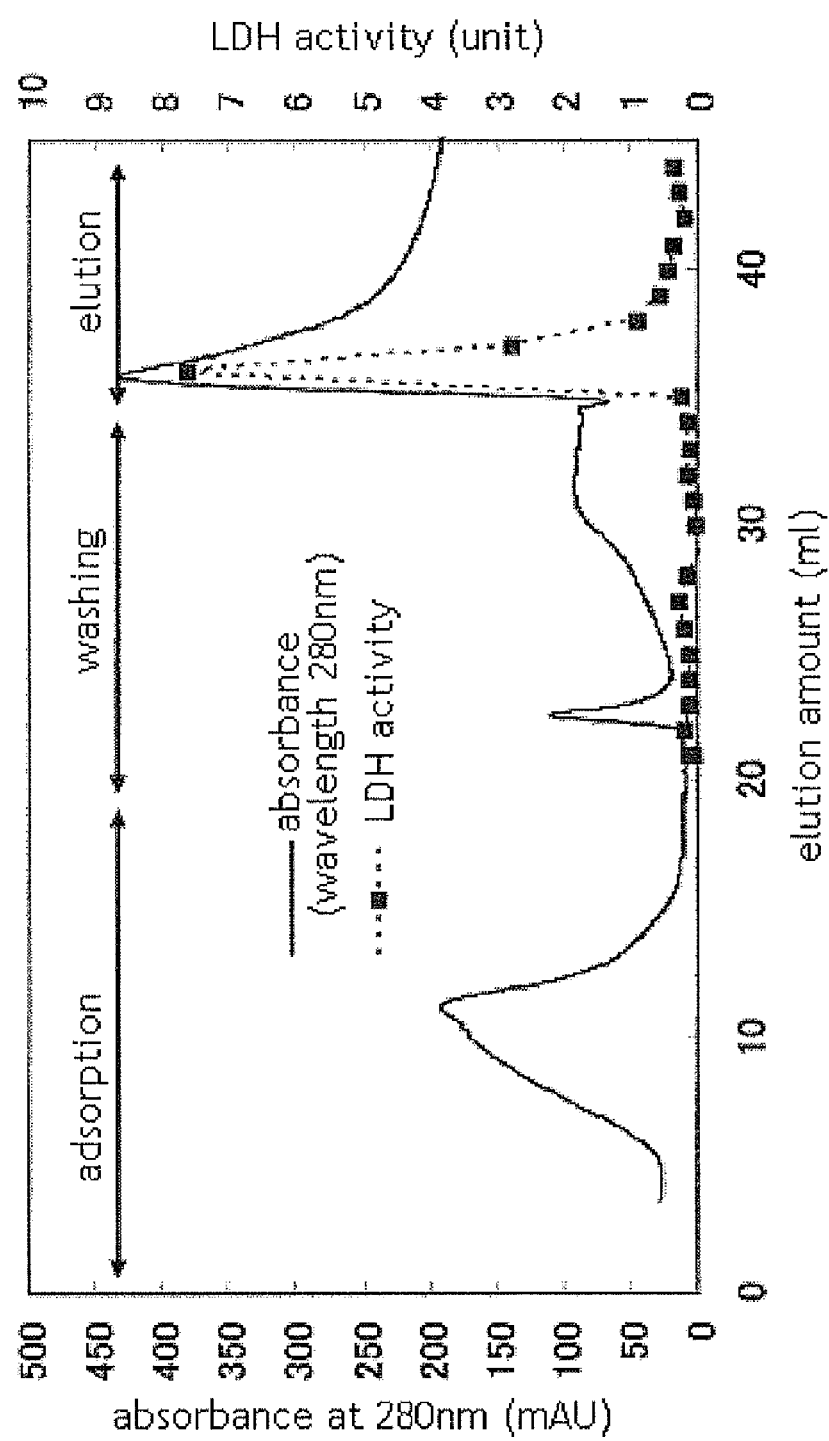
FIG. 3 shows refolding in a flow system.

The invention claimed is:

1. A protein refolding column filler, which consists of (a) zeolite with BEA structure (Zeolite Beta) that is granulated into a particle state and (b) an adhesive material for granulation of the Zeolite Beta, wherein said adhesive material is selected from the group consisting of acetylcellulose, nitrocellulose and polystyrene resin.

2. The refolding column filler according to claim 1, wherein the Zeolite Beta is granulated into particles having a particle diameter between 20 and 1,000 μm.

3. The protein refolding column filler according to claim 2 wherein the particle diameter is between 75 and 100 μm.

4. The protein refolding column filler according to claim 1, wherein the content of the adhesive material for granulation of the Zeolite Beta is 0.2% to 50% in a dry state of the adhesive material.

5. The protein refolding column filler according to claim 1, wherein the particle diameter distribution of the granulated Zeolite Beta has is controlled by regulating conditions for said granulation.

6. The protein refolding column filler according to claim 1, wherein said adhesive material is added to Zeolite Beta by spraying or dropping it to the material powders of the Zeolite Beta, while rotating and/or stirring them, and the obtained mixture is then granulated, so as to obtain the granulated Zeolite Beta.

7. An open column filled with the protein refolding column filler of claim 1.

8. The column according to claim 7, which is allowed to come into contact with a protein dispersed in a solution, so as to exhibit a protein-refolding function.

9. A column used in in-line incorporation, which is filled with the protein refolding column filler of claim 1.

* * * * *

UNITED STATES PATENT AND TRADEMARK OFFICE
CERTIFICATE OF CORRECTION

| | | |
|---|---|---|
| PATENT NO. | : 8,394,933 B2 | |
| APPLICATION NO. | : 12/593713 | |
| DATED | : March 12, 2013 | |
| INVENTOR(S) | : Masayuki Kawakami et al. | |

It is certified that error appears in the above-identified patent and that said Letters Patent is hereby corrected as shown below:

Title page, Item (73) should read as follows:

Assignee: FUJIFILM Corporation, Tokyo (JP) --and NATIONAL INSTITUTE OF ADVANCED INDUSTRIAL SCIENCE AND TECHNOLOGY, Tokyo (JP)--

Signed and Sealed this
Twenty-seventh Day of August, 2013

Teresa Stanek Rea
*Acting Director of the United States Patent and Trademark Office*